US00PP10847P

United States Patent [19]

Corbett et al.

[11] Patent Number: Plant 10,847

[45] Date of Patent: Apr. 6, 1999

[54] ***PAULOWNIA×ELONGATA* TREE NAMED 'CAROLONIA'**

[76] Inventors: Scot G Corbett, 1920-201 Eyrie Ct., Raleigh, N.C. 27606; Carl F Jordan; Huo Ying-Qiang, both of 1695 Spring Valley Rd., Athens, Ga. 30605

[21] Appl. No.: 972,460

[22] Filed: Nov. 15, 1997

Related U.S. Application Data

[63] Continuation of Ser. No. 413,768, Feb. 16, 1995, abandoned.

[51] Int. Cl.[6] ..... A01H 5/00

[52] U.S. Cl. ..... Plt./51.1

[58] Field of Search ..... Plt./51.1

[56] References Cited

PUBLICATIONS

Bailey, L.H. "Paulownia", The Standard Encyclopedia of Horticulture, The Macmillan Co., N.Y., p. 2488, 1935.

Huxley, A. et al. "Paulownia", The New RHS Dictionary of Gardening IV, The Stockten Press, N.Y., pp. 486–487, 1992.

*Primary Examiner*—Elizabeth Kemmerer
*Attorney, Agent, or Firm*—Rhodes, Coats & Bennett, L.L.P.

[57] ABSTRACT

A paulownia tree which combines the fast-growing characteristics of *Paulownia fortunei* and the cold tolerance of *Paulownia tomentosa*.

4 Drawing Sheets

This application is a continuation of application Ser. No. 08,413,768, filed Feb. 16, 1995, now abandoned.

FIELD OF THE INVENTION

The present invention relates to trees of the genus Paulownia.

BACKGROUND OF THE INVENTION

Trees of the genus Paulownia are native to China and Southeast Asia. Paulownia trees are characterized by large heart-shaped leaves and clusters of purplish white flowers. The paulownia tree is useful for pulp, veneer and OSB board.

Recently, efforts have been made to grow paulownia trees in the Southeastern United States as a substitute for southern yellow pine and various other forestry tree species. The paulownia tree is a relatively fast growing tree and it is therefore well-suited for growing lumber. *Paulownia tomentosa*, a slow growing variety has grown wild in North Carolina, Virginia and Kentucky for approximately 100 years. It is believed that the seed from the paulownia tree entered the United States in the 1890's when it was used as packaging for dishes shipped from China.

While paulownia trees are capable of growing in the Southeastern United States, greater tolerance for cold temperatures and faster growth rates would make the trees more useful for commercial purposes.

SUMMARY OF THE INVENTION

The present invention is a new and distinct variety of paulownia tree which combines the fast-growing characteristics of *Paulownia fortunei* and the cold tolerance of *Paulownia tomentosa*. The new paulownia tree is a hybrid resulting from the crossing of the offspring of *Paulownia fortunei* and *Paulownia tomentosa* with *Paulownia elongata*. The *Paulownia fortunei* and *Paulownia tomentosa* ordinarily bloom during the same period.

Pollen was manually collected from *Paulownia tomentosa. Paulownia fotunei* was fertilized with the collected pollen of *Paulownia tomentosa* to produce an offspring. That offspring was fertilized with pollen collected from *Paulownia elongata* to produce a new and distinct variety of Paulownia with a proposed name of *Paulownin elongata carolinia.*

The seeds were collected from this new and distinct variety of Paulownia were germinated. The new and distinct Paulownia variety was asexually reproduced in Athens, Ga. Root cuttings were made from an original seed grown tree from such germination and the root cuttings were grown in standard potting mix. The root cuttings were taken during the dormant winter period, reinitiated in a greenhouse which was held at a temperature of 85 degrees Fahrenheit. New shoots were harvested from plantlets to produce the material for micropropagation.

The new tree can be used for lumber production. It is expected that the new tree will produce up to 50 cords of lumber per acre in five years. The new tree can be grown in the same regions where southern yellow pine is currently being grown. In comparison, the loblolly pine produces about 5–7 cord per acre in the same period.

The relatively wide canopy of the tree makes it suitable for use as a shade tree and the inflorescence makes it suitable for ornamental uses. Further, the tree can be used for soil stabilization because of its extensive root system.

DETAILED DESCRIPTION OF THE VIEWS OF THE DRAWING

Figure 1:
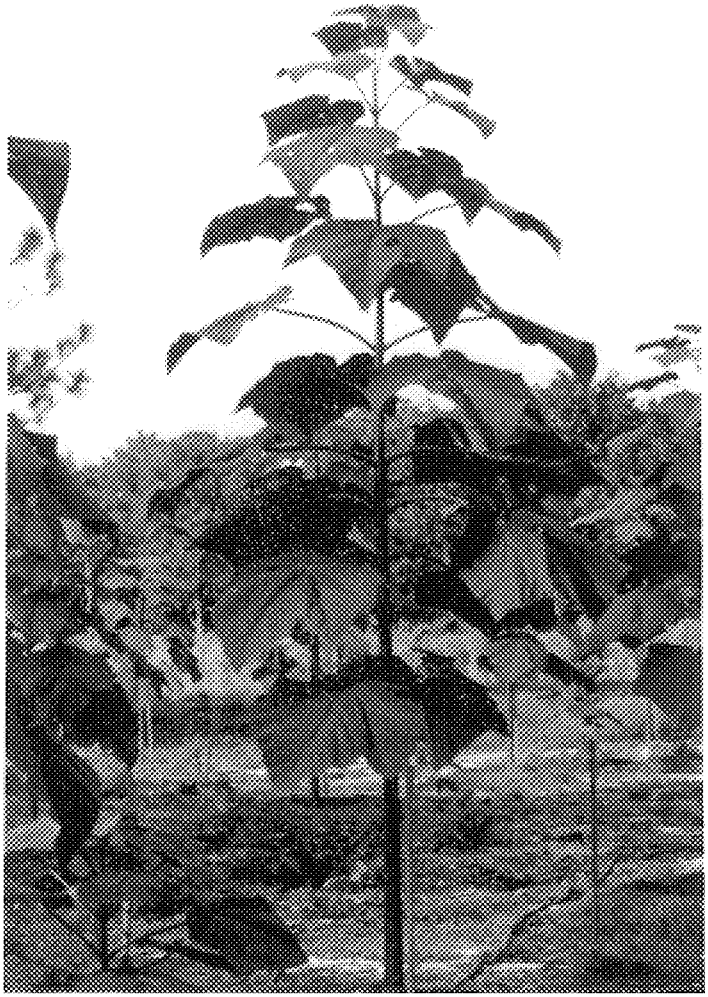
Figure 2:
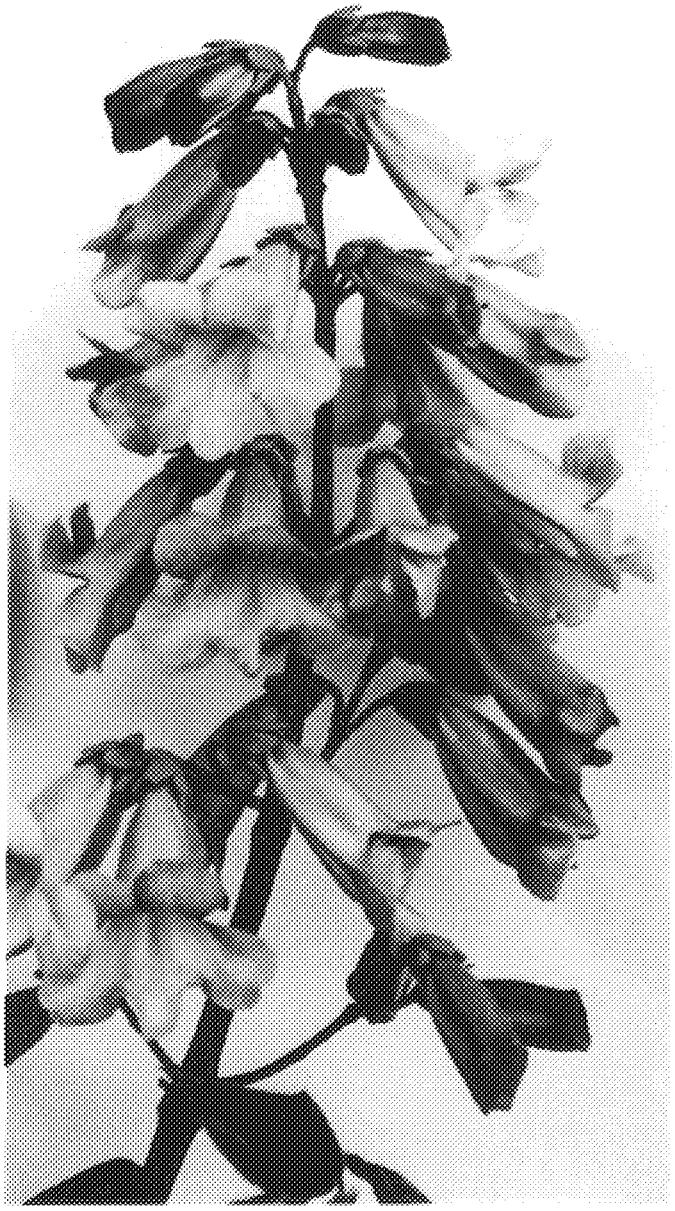
Figure 3:
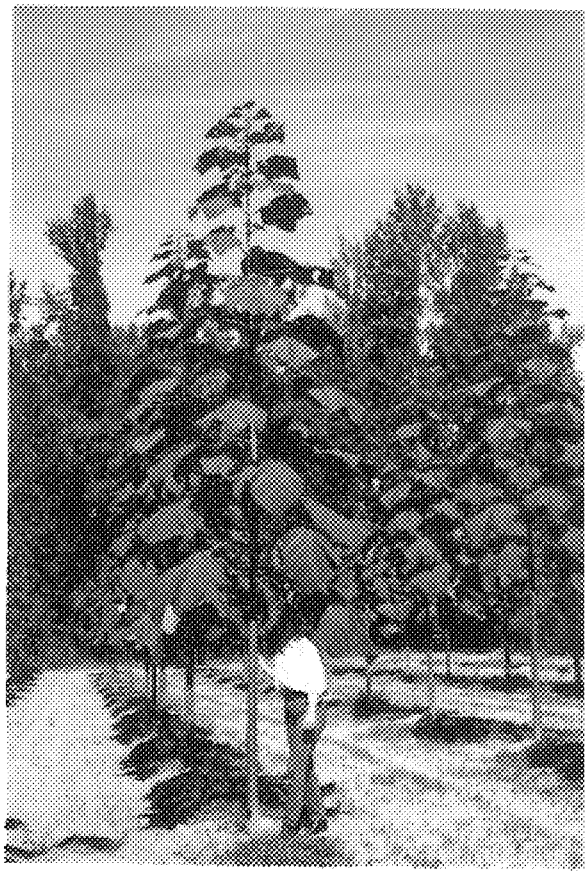
Figure 4:
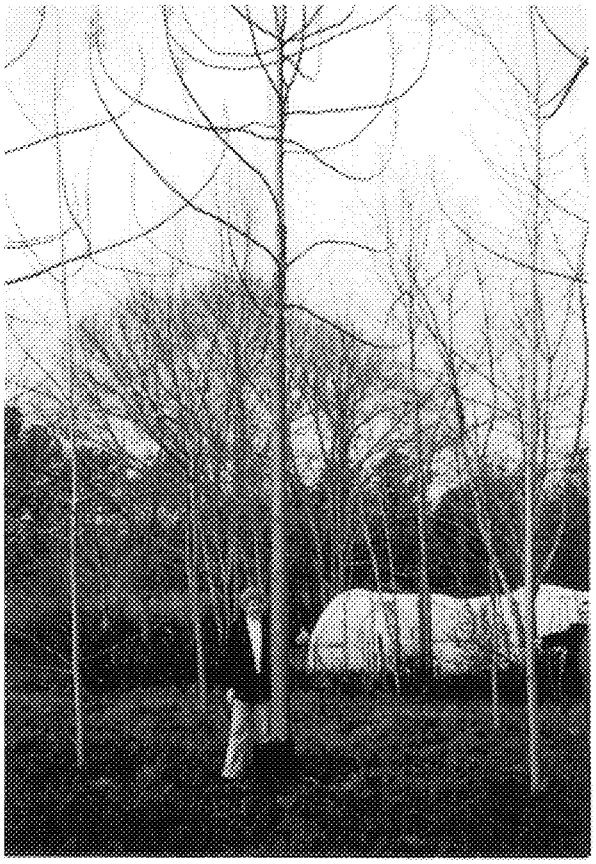

The views of the drawing include the following:

FIG. 1. A tree approximately eighteen weeks in age;

FIG. 2. A panicle of a tree approximately one year in age;

FIG. 3. A tree approximately 1 year of age, pruned for forestry application;

FIG. 4. A tree approximately 3 years of age in winter, pruned for forestry application;

BOTANICAL DESCRIPTION OF THE TREE

The color references in the following description are to The Royal Horticultural Society Colour Chart (1986 edition). The proposed name of the new tree is *Paulownia elongata carolinia.*

The *Paulownia elongata carolinia* is a deciduous tree which will reach a height exceeding 30 meters, with terate, umbrella-like crown. The new Paulownia tree is definitely recognizable. Most Paulownia species have pseudo-dichotomous branches whose terminal buds dry up and die in winter. The new and distinct variety of Paulownia tree of the present invention is exceptional in that the terminal buds often grow into new vertical growth. It has a straighter shape than *Paulownia tomentosa* and is more cold tolerant than *Paulownia fortunei*. The new variety of Paulownia will grow as far north as zone 6B as designated on the USDA plant hardiness zone map and can withstand an average annual minimum temperature of −5 degrees to −10 degrees Fahrenheit. The new Paulownia tree is exceptionally drought tolerant and can be cultivated in area with between 100 and 150 millimeters of rain annually. Supplemental irrigation may be required in the first 9–12 weeks of growth. The new tree has a deep tap root and an extensive lateral root system with 60% of the system 20 to 30 inches below the surface.

Flowers: The inflorescence is a cyme or two to five flowers approximately 2 inches in length which may be pedunculate or subsessile. They are produced in the axils of diminutive or smaller leaves in summer and autumn. The flowers are pedicellate and articulate at the apical end and emerge in March and April. The calyx is fleshy, companulate and unequally 5-lobed. The lobes are triangular, with the upper middle lobe slightly larger and densely covered in fine hairs. The hairs fall at anthesis. The corolla is big and color varies from white (155D) to mauve (72A) intensity depending on soil conditions. The corolla is two-lipped with two lobes on the upper lip and three elongated lobes on the lower lip. The companulate corolla tube is usually curved forward 5 millimeters from the base after which it enlarges gradually. Inside the corolla lower half there are usually clear ribs tinted with yellow. The 4 stamens are didynamous about half as long as the corolla. The ovary is bilocular and pistil is generally as long as the stamens. Flower buds gray-green in color are formed in autumn, remain naked over winter, and blossom out in spring (March/April). The length of the cymes with or without peduncles the depth of the calyx lobe, the shape and colors of the corolla and capsule distinguish the Paulownia tree from *Paulownia fortunei* and *Paulownia tomentosa.*

Fruits: The fruits are loculicidal capsules, ellipsoid, ovoid or subglobose in shape. Capsules mature in September, October and November and are usually less than 6 cm long, whereas in *Paulownia tomentosa* and *Paulownia fortunei* they are greater than 6 cm.

Bark: Bark is more green than that of *Paulownia tomentosa* and more gray than that of *Paulownia fortunei,* with a color chart designation of 197-A, and varies in thickness from 1/16th to 1/8th inch with a smooth surface.

Foliage: The leaves are large 24"–36" in diameter in juvenile phase (8 to 10 inches in mature individuals), cordate with a smooth to wavy margin. The leaf is more pubescent than *Paulownia fortunei* but less than *Paulownia tomentosa*. The leaves are dark to light green (between 139B to 139C). The venation is palmate. Fall leaf coloration changes from green to black at first frost. *Paulownia tomentosa* and *Paulownia fortunei* are recorded as long living trees. It is expected that this new Paulownia tree will have a life expectancy exceeding 100 years.

Buds: Most Paulownia species have pseudo-dichotomous branches whose terminal buds dry up after winter, and whose lateral buds are equally dominant, with the result being a short stem with an open crown. *Paulownia elongata carolnia*, however, like *Paulownia fortunei* produces one dominant and one sub-dominant bud, resulting in a stem with a straighter shape.

Form and branching characteristics: The tree is generally cylindrical in form, whether grown in isolation or in monoculture in a forest, and has a terate, umbrella-like crown. The primary and secondary branching is opposite. The branches form in pairs along the trunk and the branches in each pair are disposed 180 degrees apart. The pairs of branches are spaced approximately 8 to 10 inches apart and produce a dense canopy. The branch pairs are disposed at approximately 90 degrees to the adjacent branch pairs. The normal angle of the scaffold branches is approximately 90 degrees relative to the trunk. The scaffold branches begin at slightly above ground level in the absence of pruning. Bark inclusions are formed in the crotches of the scaffold branches.

Tolerance: *Paulownia elongata carolinia* is more cold tolerant than *Paulownia fortunei*, and will grow well as far north as zone 6-B, as designated on the U.S.D.A. plant hardiness zone map. It can withstand an average annual minimum temperature of 0° to −5° F., and is suitable for planting as far north as Maryland. It is more drought tolerant than either *Paulownia tomentosa* or *Paulownia fortunei*. Selection has been made for exceptional drought tolerance, and it can be cultivated in areas with between 50 and 100 mm of rain annually, such as occur in Kansas. *Paulownia elongata carolinia* combines the fast-growing characteristics of *Paulownia forfunei* and the cold tolerance of *Paulownia tomentosa*. Pollen was manually collected from *Paulownia tomentosa. Paulownia fortunei* was fertilized with the collected pollen of *Paulownia tomentosa* to produce an offspring. The offspring was fertilized with pollen collected from *Paulownia elongata* thus producing a new and distinct variety of Paulownia tree. The seeds were collected from this new and distinct variety of Paulownia and were germinated. The new and distinct Paulownia variety was asexually reproduced in Athens, Ga. Root cuttings were made from an original seed grown tree and the root cuttings were grown in a standard potting mix. Root cuttings were taken during the dormant winter period, reinitiated in a greenhouse which was held at a temperature of 85 degrees Fahrenheit. The new shoots were harvested from plantlets to produce the material for micropropagation.

What is claimed is:

1. A new and distinct variety of Paulownia tree as shown and described, which combines the fast-growing characteristics of *Paulownia fortunei* and the cold tolerance of *Paulownia tomentosa*.

* * * * *